United States Patent [19]
Aoki et al.

[11] 4,085,207
[45] Apr. 18, 1978

[54] AMINO ACID PARENTERAL SOLUTION CONTAINING REDUCING SUGAR

[75] Inventors: Mitsuo Aoki; Kazuhiko Watanabe; Shunichi Murase, all of Maruto; Isao Hiraoka, Tokushima, all of Japan

[73] Assignee: Otsuka Pharmaceutical Factory, Inc., Japan

[21] Appl. No.: 670,070

[22] Filed: Mar. 24, 1976

[30] Foreign Application Priority Data

Apr. 1, 1975    Japan ................................. 50-40072

[51] Int. Cl.$^2$ ...................... A61K 31/70; A61K 31/40
[52] U.S. Cl. .................................. 424/180; 424/274; 424/319
[58] Field of Search ...................... 424/274, 319, 180

[56] References Cited

U.S. PATENT DOCUMENTS

| 2,411,897 | 12/1946 | Sahyun | 424/319 |
| 3,080,234 | 3/1963 | Jarowski | 424/319 X |
| 3,697,287 | 10/1972 | Winitz | 424/319 X |

OTHER PUBLICATIONS

Chemical Abstracts, 60:1960f, (1964).

*Primary Examiner*—Leonard Schenkman
*Attorney, Agent, or Firm*—McGlew and Tuttle

[57] ABSTRACT

An amino acid parenteral solution containing at least one of N-acyl-L-tryptophans and N-acyl-L-prolines, and at least one reducing sugar.

4 Claims, No Drawings

AMINO ACID PARENTERAL SOLUTION CONTAINING REDUCING SUGAR

This invention relates to an amino acid parenteral solution containing a reducing sugar.

When the living body fails to orally ingest proteins due to a gastrointestinal disorder or some other cause, it is required to give the living body amino acids by injection in order to maintain the body in nitrogen equilibrium for the synthesis of proteins in vivo. However the administered amino acids tend to be partially utilized as a source of energy instead of being used for the synthesis of proteins. This tendency becomes pronounced when the energy in the living body is insufficient. Accordingly it is desirable, and hence attempted, for effective use of amino acids to prepare an amino acid parenteral solution containing glucose, fructose, maltose or the like reducing sugar. However, during sterilization in the course of preparation as well as during storage, the reducing sugar undergoes the Maillard reaction with amino acids, giving a brown reaction product which impairs the stability of the solution. Thus the sugar-containing amino acid parenteral solution remains yet to be develped and, at present, a solution of reducing sugar is admixed with the amino acid solution immediately before use. This method has the drawbacks that the procedure is cumbersome and that the ratio of the reducing sugar to the amino acids is not always constant. It is therefore desired to provide an amino acid parenteral solution incorporating a reducing sugar which solution can be preserved over a prolonged period of time in a stable state.

The primary object of this invention is to provide an amino acid parenteral solution which is entirely free of the above-mentioned drawbacks heretofore encountered.

Another object of this invention is to provide an amino acid parenteral solution containing a reducing sugar which can be prepared free of the Maillard reaction and which is stable over a prolonged period of preservation.

Other objects and features of this invention will become apparent from the following description.

This invention provides amino acid parenteral solutions containing at least one of N-acylated L-tryptophans and N-acylated L-prolines, and at least one reducing sugar.

Our research has revealed that when an amino acid parenteral solution containing N-acyl-L-tryptophan and/or N-acyl-L-proline as amino acids further incorporates a reducing sugar therein, the solution does not undergo the Maillard reaction during sterilization at high temperatures and remains very stable during a prolonged period of preservation. This invention has been accomplished based on this novel finding.

The N-acylated L-tryptophans and N-acylated L-prolines to be used in this invention are those having various physiological acid residues. Examples of the acids useful for the acylation are:

(1) Fatty acids including monovalent saturated fatty acids such as acetic acid, caproic acid, palmitic acid and stearic acid; bivalent saturated fatty acids such as malonic acid and succinic acid, monovalent unsaturated fatty acids such as oleic acid, linoleic acid and linolenic acid, and bivalent unsaturated fatty acids such as fumaric acid and maleic acid.

(2) Aromatic carboxylic acids such as benzoic acid, phenylacetic acid and phenoxyacetic acid.

(3) Aliphatic oxy acids such as lactic acid and malic acid.

(4) Aliphatic keto-acids such as pyruvic acid and acetacetic acid.

(5) Amino acids such as glycine and leucine.

(6) Polyoxycarboxylic acids such as gluconic acid, etc.

The acylation is conducted in a usual manner, for example, by adding a corresponding acid anhydride or acid chloride to an amino acid solution.

Examples of the N-acyl-L-tryptophans useful in this invention are N-acetyl-L-tryptophan, N-lactyl-L-tryptophan, N-phenylacetyl-L-tryptophan, N-phenoxyacetyl-L-tryptophan, N-carbobenzoxy-L-tryptophan, N-oleyl-L-tryptophan, N-maleyl-L-tryptophan, N-benzoyl-L-tryptophan, N-glycyl-L-tryptophan, N-leucyl-L-tryptophan, etc. Examples of N-acyl-L-prolines are N-acetyl-L-proline, N-lactyl-L-proline, N-phenylacetyl-L-proline, N-phenoxyacetyl-L-proline, N-benzoyl-L-proline, N-carbobenzoxy-L-proline, N-valyl-L-proline, N-maleyl-L-proline, N-oleyl-L-proline, N-glycyl-L-proline, N-leucyl-L-proline, etc. Among these examples, preferable are N-acetyl-L-tryptophan, N-lactyl-L-tryptophan, N-phenylacetyl-L-tryptophan, N-carbobenzoxy-L-tryptophan, N-leucyl-L-tryptophan, N-acetyl-L-proline, N-phenylacetyl-L-proline, N-lactyl-L-proline, N-carbobenzoxy-L-proline and N-valyl-L-proline.

The concentration of these N-acylated L-tryptophans and L-prolines in the parenteral solution is usually 0.06 to 0.4 W/V%, more preferably 0.07 to 0.3 W/V%.

The parenteral solution of this invention containing the N-acyl-L-tryptophan and/or N-acyl-L-proline may further incorporate therein at least one of essential amino acids such as L-arginine, L-histidine, L-leucine, L-isoleucine, L-methionine, L-lysine, L-phenylalanine, L-threonine and L-valine and salts thereof, and dispensable amino acids such as L-serine, L-aspartic acid, L-glutamic acid, L-tyrosine, L-cystine, L-alanine and glycine and salts thereof. These amino acids and salts may be used as N-acylated with the same physiological acid in the same manner as in the case of L-tryptophan and L-proline, whereby the parenteral solution can be greatly improved in stability. The concentration of such amino acids and salts thereof in the solution is usually about 3 to about 12 W/V%.

The reducing sugars usable in this invention include glucose, fructose, maltose, lactose, etc., at least one of which is added to the parenteral solution in a concentration of usually about 3 to about 25 W/V%. The concentration in excess of 25 W/V% causes browning phenomenon in the parenteral solution when sterilized with steam, while at the concentration of less than 3 W/V% it is difficult to fully achieve the objects of this invention. Preferably, the concentration of reducing sugar is about 5 to about 20 W/V%.

The parenteral solution of this invention is prepared in the usual manner by dissolving the desired amino acids and reducing sugar in pure water, filtering the solution, placing the resulting solution into vials and thereafter sterilizing the solution with steam.

The parenteral solution of this invention is substantially free of the browning phenomenon due to the Maillard reaction even when sterilized at high temperatures. To confirm such outstanding effect, N-acyl-L-tryptophan or N-acyl-L-proline are added, in varying concentrations, to a 5 W/V% aqueous solution of glucose, sterilizing the solutions at 110° C for 60 minutes with steam and checking the solutions for transparency with the unaided eye and for transmittance by spectrophotometer. The results are given in Table 1.

Table 1

| Compound | Concn. (%) | Appearance | Transmittance (%) (420mµ) |
|---|---|---|---|
| N-Acetyl-L-tryptophan | 0.072 | Colorless, transparent | 95.9 |
| N-Lactyl-L-tryptophan | 0.081 | Colorless, transparent | 96.3 |
| N-Phenylacetyl-L-tryptophan | 0.095 | Colorless, transparent | 99.6 |
| N-Phenoxyacetyl-L-tryptophan | 0.099 | Colorless, transparent | 96.7 |
| N-Maleyl-L-tryptophan | 0.089 | Colorless, transparent | 98.2 |
| N-Glycyl-L-tryptophan | 0.076 | Colorless, transparent | 97.3 |
| N-Leucyl-L-tryptophan | 0.093 | Colorless, transparent | 95.7 |
| N-Acetyl-L-proline | 0.123 | Colorless, transparent | 99.3 |
| N-Lactyl-L-proline | 0.15 | Colorless, transparent | 99.5 |
| N-Phenylacetyl-L-proline | 0.18 | Colorless, transparent | 99.4 |
| N-Phenoxyacetyl-L-proline | 0.19 | Colorless, transparent | 99.0 |
| N-Carbobenzoxy-L-proline | 0.19 | Colorless, transparent | 99.4 |
| N-Glycyl-L-proline | 0.14 | Colorless, transparent | 98.9 |
| N-Leucyl-L-proline | 0.18 | Colorless, transparent | 97.9 |

For a better understanding of this invention, examples are given below.

EXAMPLE 1

| L-Arginine hydrochloride | 2.36 g |
|---|---|
| L-Histidine hydrochloride | 2.20 g |
| L-Leucine | 2.94 g |
| L-Isoleucine | 2.10 g |
| L-Methionine | 1.50 g |
| L-Lysine hydrochloride | 2.93 g |
| L-Phenylalanine | 2.55 g |
| L-Threonine | 1.56 g |
| L-Valine | 1.80 g |
| N-Acetyl-L-tryptophan | 0.72 g |
| N-Acetyl-L-proline | 1.23 g |
| L-Serine | 1.20 g |
| L-Aspartic acid | 2.10 g |
| L-Glutamic acid | 3.60 g |
| L-Tyrosine | 0.15 g |
| L-Cystine | 0.06 g |
| L-Alanine | 1.44 g |
| Glycine | 2.46 g |
| Glucose | 50.00 g |

The above compounds are added to deionized water to prepare 1,000 ml of a solution, which is filtered, placed in 500-ml vials, sealed and sterilized with high-pressure steam at 110° C for 60 minutes to obtain an amino acid parenteral solution containing glucose.

EXAMPLE 2

In the same manner as in Example 1 except that 0.77 g of N-glycyl-L-tryptophan and 1.35 g of N-glycyl-L-proline are used in place of 0.72 g of N-acetyl-L-tryptophan and 1.23 g of N-acetyl-L-proline, amino acid parenteral solution containing glucose is prepared.

EXAMPLE 3

In the same manner as in Example 1 except that 50 g of fructose is used in place of 50 g of glucose, amino acid parenteral solution is prepared which contains fructose.

EXAMPLE 4

The same procedure as in Example 1 is repeated except that 100 g of maltose is used in place of 50 g of glucose to prepare an amino acid parenteral solution containing maltose. After sterilization, the solution is examined by spectrophotometer for changes in transmittance at 420 mµ with the lapse of time. The results are given in Table 2.

Table 2

| Days elapsed | 0* | 2 | 6 | 15 | 30 | 60 |
|---|---|---|---|---|---|---|
| Transmittance (%) | 98.2 | 97.7 | 97.0 | 96.9 | 96.5 | 95.2 |

*Immediately after sterilization.

COMPARISON EXAMPLE

The same procedure as in Example 1 is repeated except that 0.6 g of L-tryptophan is used in place of 0.72 g of N-acetyl-L-tryptophan, and 0.9 g of L-proline in place of 1.23 g of N-acetyl-L-proline to prepare 1,000 ml of a solution, which is sterilized in the same manner as in Example 1 to obtain an amino acid parenteral solution containing glucose.

The amino acid parenteral solutions prepared in Examples 1 – 4 and Comparison Example are examined immediately after sterilization for appearance with the unaided eye and also for transmittance at 420 mµ by spectrophotometer. The results are listed in Table 3.

Table 3

| Parenteral solution | Appearance | Transmittance at 420 mµ (%) |
|---|---|---|
| Example 1 | Colorless, transparent | 97.2 |
| Example 2 | Colorless, transparent | 98.1 |
| Example 3 | Colorless, transparent | 97.4 |
| Example 4 | Colorless, transparent | 98.2 |
| Comparison Example | Reddish brown liquid with blackish brown precipitate | — |

As will be apparent from Tables 2 and 3, the parenteral solutions of this invention remain stable for a prolonged period of preservation and also exhibit good stability free of any browning phenomenon when sterilized with steam.

EXAMPLE 5

In the same manner as in Example 1 except that 0.95 g of N-phenylacetyl-L-tryptophan and 1.80 g of N-phenylacetyl-L-proline are used in place of 0.72 g of N-acetyl-L-tryptophan and 1.23 g of N-acetyl-L-proline, amino acid parenteral solution containing glucose is prepared.

EXAMPLE 6

In the same manner as in Example 1 except that 0.99 g of N-carbobenzoxy-L-tryptophan and 1.90 g of N-carbobenzoxy-L-proline are used in place of 0.72 g of N-acetyl-L-tryptophan and 1.23 g of N-acetyl-L-proline, amino acid parenteral solution containing glucose is prepared.

EXAMPLE 7

In the same manner as in Example 1 except that 0.93 g of N-leucyl-L-tryptophan and 1.70 g of N-valyl-L-proline are used in place of 0.72 g of N-acetyl-L-tryptophan and 1.23 g of N-acetyl-L-proline, amino acid parenteral solution containing glucose is prepared.

EXAMPLE 8

Glucose and N-phenylacetyl-L-tryptophan are added to deionized water to prepare an amino acid parenteral solution containing 5.0 W/V% of glucose and 0.095 W/V% of N-phenylacetyl-L-tryptophan.

EXAMPLE 9

Glucose and N-phenylacetyl-L-proline are added to deionized water to prepare an amino acid parenteral solution containing 5.0 W/V% of glucose and 0.18 W/V% of N-phenylacetyl-L-proline.

The amino acid parenteral solutions prepared in Examples 5 – 9 are examined immediately after sterilization for appearance with the unaided eye and also for transmittance at 420 mμ by spectrophotometer. Table 4 below shows the results.

Table 4

| Solution | Appearance | Transmittance at 420 mμ (%) |
|---|---|---|
| Ex. 5 | Colorless, transparent | 96.2 |
| 6 | " | 96.2 |
| 7 | " | 97.4 |
| 8 | " | 99.6 |
| 9 | " | 99.4 |

What we claim is:

1. A heat sterilized amino acid parenteral solution containing from about 0.06 to about 0.4 W/V% of a mixture of (i) at least one N-acyl-L-tryptophan and at least one N-acyl-L-proline, and (ii) from about 3 to about 25 W/V% of at least one reducing sugar, said N-acyl-L-tryptophan being at least one species selected from the group consisting of N-acetyl-L-tryptophan, N-lactyl-L-tryptophan, N-phenylacetyl-L-tryptophan, N-phenoxyacetyl-L-tryptophan, N-carbobenzoxy-L-tryptophan, N-oleyl-L-tryptophan, N-maleyl-L-tryptophan, N-benzoyl-L-tryptophan, N-glycyl-L-tryptophan and N-leucyl-L-tryptophan, said N-acyl-L-proline being at least one species selected from the group consisting of N-acetyl-L-proline, N-lactyl-L-proline, N-phenylacetyl-L-proline, N-phenoxyacetyl-L-proline, N-benzoyl-L-proline, N-carbobenzoxy-L-proline, N-valyl-L-proline, N-maleyl-L-proline, N-oleyl-L-proline, N-glycyl-L-proline and N-leucyl-L-proline, said reducing sugar being at least one species selected from the group consisting of glucose, fructose, maltose and lactose.

2. The amino acid parenteral solution according to claim 1, in which said N-acyl-L-tryptophan is at least one species selected from the group consisting of N-acetyl-tryptophan, N-lactyl-L-tryptophan, N-phenylacetyl-L-tryptophan, N-carbobenzoxy-L-tryptophan and N-leucyl-L-tryptophan.

3. The amino acid parenteral solution according to claim 1, in which the concentration of said mixture of (i) is 0.07 to 0.3 W/V%.

4. The amino acid parenteral solution according to claim 1, in which the concentration of the reducing sugar (ii) is about 5 to about 20 W/V%.

* * * * *